(12) United States Patent
Jabri et al.

(10) Patent No.: US 9,118,635 B2
(45) Date of Patent: Aug. 25, 2015

(54) MEDICAL IMAGING SYSTEM

(75) Inventors: Kadri Nizar Jabri, Waukesha, WI (US);
Rajeev Ramankutty Marar, Waukesha, WI (US); Ferry Tamtoro, Oconomowoc, WI (US); Gopal Biligeri Avinash, Menomonee Falls, WI (US); John Michael Sabol, Sussex, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 982 days.

(21) Appl. No.: 11/934,338

(22) Filed: Nov. 2, 2007

(65) Prior Publication Data

US 2009/0118606 A1    May 7, 2009

(51) Int. Cl.
G06K 9/00     (2006.01)
H04L 29/08    (2006.01)
G06F 19/00    (2011.01)
G06Q 50/22    (2012.01)

(52) U.S. Cl.
CPC .............. H04L 67/06 (2013.01); G06F 19/321 (2013.01); G06Q 50/22 (2013.01)

(58) Field of Classification Search
USPC .................. 382/128–134; 378/1–90
See application file for complete search history.

(56) References Cited

U.S. PATENT DOCUMENTS

| 4,709,382 | A  | * | 11/1987 | Sones ............................. 378/62 |
| 6,325,540 | B1 |   | 12/2001 | Lounsberry et al. |
| 6,529,618 | B1 | * | 3/2003  | Ohara et al. .................. 382/132 |
| 6,542,846 | B1 | * | 4/2003  | Miller et al. .................. 702/132 |
| 7,090,396 | B2 |   | 8/2006  | Boomgaarden |
| 2004/0088193 | A1 | * | 5/2004 | Moriyama et al. ................ 705/3 |
| 2005/0105788 | A1 | * | 5/2005 | Turek et al. .................... 382/131 |
| 2006/0008053 | A1 | * | 1/2006 | Ishikawa et al. ............. 378/111 |
| 2008/0078939 | A1 | * | 4/2008 | Hennessy et al. ........ 250/370.09 |

FOREIGN PATENT DOCUMENTS

| JP | 08336516 A | 12/1996 |
| JP | 2002191586 A | 7/2002 |
| JP | 2002224095 A | 8/2002 |
| JP | 2003024317 A | 1/2003 |
| JP | 2005176990 A | 7/2005 |
| JP | 2006204756 A | 8/2006 |
| JP | 2006263325 A | 10/2006 |

OTHER PUBLICATIONS

Preliminary Search Report for FR 08 57443; search achieved Dec. 13, 2013; 5 pages.
JP Office Action; JP Application #2008-277635; mailed Apr. 8, 2014.

* cited by examiner

*Primary Examiner* — Alex Liew
(74) *Attorney, Agent, or Firm* — Fletcher Yoder, P.C.

(57) ABSTRACT

An autonomous medical imaging system includes at least one autonomous imaging subsystem and at least one autonomous detection subsystem. The autonomous detection subsystem is configured to communicate with the autonomous imaging subsystem, and the autonomous imaging subsystem is configured to communicate with the autonomous detection subsystem.

15 Claims, 2 Drawing Sheets

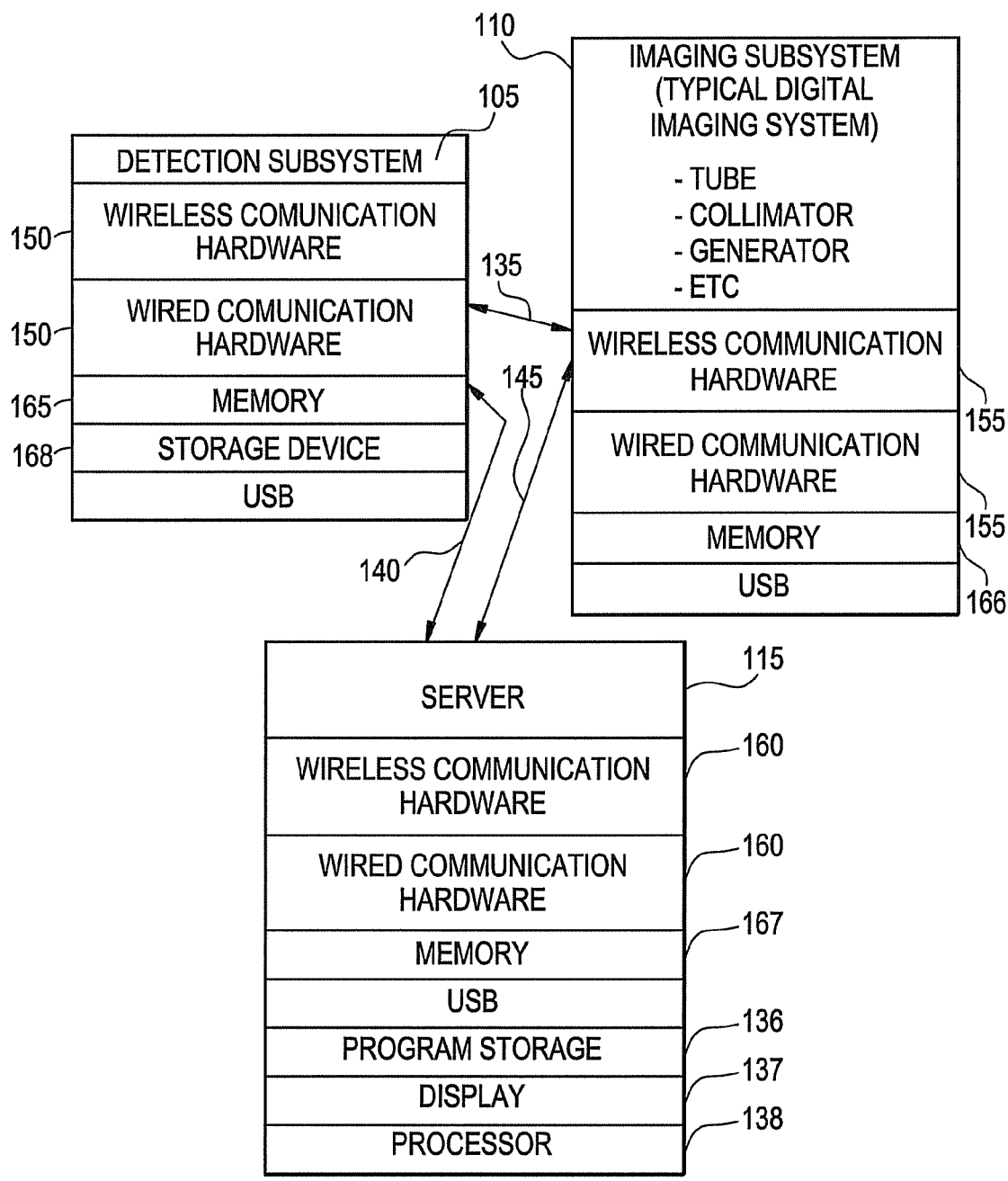

MEDICAL IMAGING SYSTEM

BACKGROUND OF THE INVENTION

The present disclosure relates generally to imaging systems, and particularly to imaging systems using digital detectors.

The advent of digital detectors has brought enhanced workflow and high image quality to medical imaging, such as mobile or portable radiology. In current state of the art medical imaging environments, an imaging system includes an imaging subsystem and a detector. Current imaging subsystems are calibrated for and permanently integrated with specific detectors, such that detectors cannot function without the integrated imaging subsystem. Similarly, without the integrated detector, the imaging subsystem is not functional. Additionally, current detectors and imaging subsystems have limited data transfer capabilities which restrict non-native compatibility between detectors and imaging subsystems that were not originally integrated together.

Accordingly, even if the imaging system includes an imaging subsystem using a detachable or wireless detector, the detector is typically restricted to use with the specific imaging subsystem (and corresponding clinical applications) with which it has been integrated. For example, the imaging subsystem usually needs to be aware of detector-specific functionally descriptive properties, such as calibration files, electronic readout speed, and defective pixel location for example, in order to produce acceptable images.

Furthermore, clinical applications are enabled on the imaging system as a function of the detector and imaging subsystem capabilities and options that are purchased by the customer. In normal operation the detectors and applications are fixed as a static list and will not change. Therefore, purchase of a new clinical application requires service, such as a detector upgrade, software, and hardware changes that the customer is typically unable to provide.

Accordingly, there is a need in the art for an imaging system arrangement that overcomes these drawbacks.

BRIEF DESCRIPTION OF THE INVENTION

An embodiment of the invention includes an autonomous medical imaging system including at least one autonomous imaging subsystem and at least one autonomous detection subsystem. The autonomous detection subsystem is configured to communicate with the autonomous imaging subsystem, and the autonomous imaging subsystem is configured to communicate with the autonomous detection subsystem.

Another embodiment of the invention includes an autonomous detection subsystem for use with an autonomous medical imaging system. The autonomous detection subsystem is configured to communicate with at least one autonomous imaging subsystem.

Another embodiment of the invention includes an autonomous imaging subsystem for use with an autonomous medical imaging system. The autonomous imaging subsystem is configured to communicate with at least one autonomous detector subsystem.

These and other advantages and features will be more readily understood from the following detailed description of preferred embodiments of the invention that is provided in connection with the accompanying drawings.

BRIEF DESCRIPTION OF THE DRAWINGS

Referring to the exemplary drawings wherein like elements are numbered alike in the accompanying Figures:

FIGS. 1 through 3 depict autonomous imaging systems in accordance with embodiments of the invention.

DETAILED DESCRIPTION OF THE INVENTION

An embodiment of the invention leverages growth of computer networking technology and provides an autonomous imaging system capable to establish an association between an autonomous imaging subsystem and an autonomous detector subsystem without a permanent integration of the autonomous imaging subsystem and autonomous detector subsystem. This capability provides flexibility for accommodating replacement of either of the autonomous detector subsystem or the imaging subsystem in a dynamic imaging environment.

As used herein, the phrase "autonomous system" describes a system that has communication capability even when it is not connected or associated with a specific autonomous imaging subsystem. Further, the phrase "autonomous detection subsystem" describes a detection system that has communication capability with a network, such as server, even when it is not connected or associated with a specific imaging subsystem. Further, the autonomous detection subsystem provides communication capability (such as with a second autonomous imaging subsystem or a second network) even when it is associated with one autonomous imaging subsystem.

Stated alternatively an embodiment of the invention provides autonomous imaging components in terms of system design, system implementation, application deployment, and service. As such, the autonomous components are configured for and capable of use with more than one other mating, complementary autonomous component. Accordingly, each of the main components, the autonomous imaging subsystem and the autonomous detector subsystem, are considered as network nodes that operate as autonomous entities in a network environment. In this environment, it is contemplated that multiple types of autonomous detector subsystems, such as from the same or different vendors, based on capability, and sizes for example, can be used with multiple types of imaging subsystems.

Figure 1:
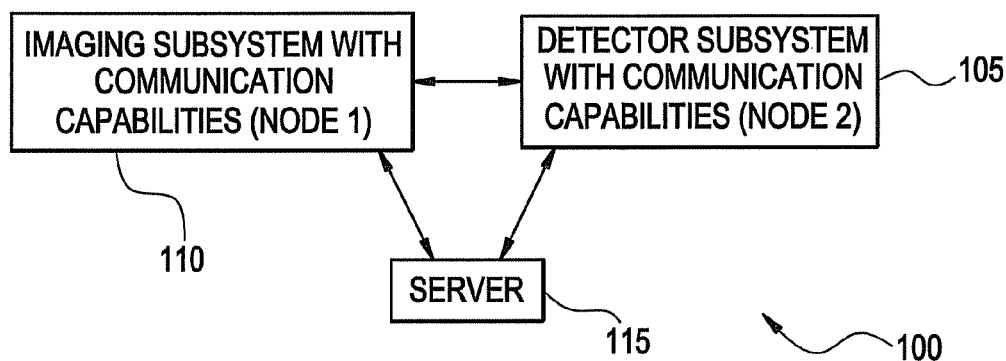

Referring to FIG. 1, an embodiment of an autonomous medical imaging system 100, such as a network environment for example, is depicted in block form. The autonomous imaging system 100 includes an autonomous detection subsystem 105 (also herein referred to as a "detector") and autonomous imaging subsystem 110 (also herein referred to as an "imaging subsystem"). In one embodiment, the autonomous imaging system 100 includes the imaging subsystem 110 (exclusive of the detector 105) as a first network node and the detector 105 (exclusive of the imaging subsystem 110) as a second network node. The imaging subsystem 110 and the detector subsystem 105 each include communication capabilities such that they can each operate or communicate with at least one other autonomous subsystem 105, 110 independent of each other, in addition to being able to operate or communicate with each other. In one embodiment, the detector 105 is configured to communicate with the imaging subsystem 110, and the imaging subsystem 110 is configured to communicate with the detector 105 via a network. In another embodiment, the detector 105 is configured to communicate with the imaging subsystem 110, and the imaging subsystem 110 is configured to communicate with the detector 105 via a global communication network, such as the Internet, for example.

An embodiment of the autonomous imaging system 100 also includes a server 115 coupled to, or in communication with, at least one of the first network node of the imaging subsystem 110 and the second network node of the detector subsystem 105.

In an embodiment, direct communication between the detector 105 and the server 115 allows unimpeded detector 105 data storage, registration, and location identification while the detector 105 is not being used with the imaging subsystem 110 for imaging. In a similar fashion, direct communication between the imaging subsystem 110 and the server 115 allows determining, by the server 115, of a suitable detector 105 for a particular application, as well as transfer of calibration files, software, and firmware upgrades for example.

Figure 2:
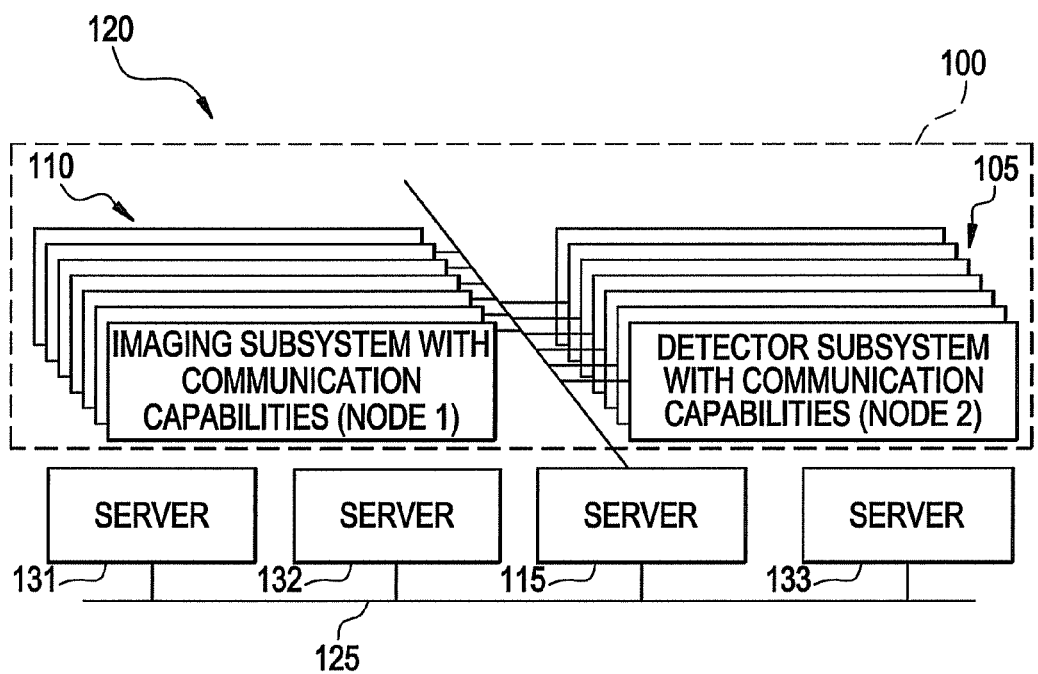

Referring now to FIG. 2, an embodiment of a distributed network system 120 is depicted. In an embodiment, the autonomous imaging system 100 includes more than one imaging subsystem 110 and detector 105 in signal communication with the server 115. In an embodiment, the server 115 is in signal communication via a distributed network 125 such as a hospital network 125 for example, with servers 131-133, which can include additional servers 115 as well as servers 131-133 having other functions, as will be described further below. Furthermore, by communicating with one or more detectors 105 and one or more imaging subsystems 110, the server 115 maintains standardized image acquisition protocols including calibration procedures and methods through out the hospital network 125. In an embodiment, the hospital network 125 includes a connection to the Internet, to thereby allow remote access to the autonomous imaging system 100 to transfer data for remote diagnostic and service upgrade purposes for example.

Referring now to FIG. 3, an embodiment of the autonomous imaging system 100, providing greater detail related to the individual components 105, 110, 115 is depicted in block form. A purpose of the autonomous imaging system 100 in addition to normal imaging tasks, is to provide access to shared resources, such as data and information related to the subsystems 105, 110 that may reside on the server 115.

In an embodiment the server 115 includes a program storage device 136 to store system, data, application, and electronic communication files, an output device, such as a CRT display screen 137, configured to display server 115 settings and a processor 138.

Autonomous imaging subsystems 110 and detectors 105 can be configured to communicate with each other via primary-networking components such as network interconnection 135, via means such as copper wire, fiber optic cable, infrared and radio connections for example, providing communication between the subsystems 105, 110. Similarly, autonomous imaging subsystems 110 and autonomous detection subsystems 105 can be configured to communicate with the server 115 via network interconnections 140, 145 For example, each component 105, 110, 115 includes Network Interface Circuitry (NIC) 150, 155, 160 (also herein referred to as an "interface") connectable with the system 100 to support system 100 communication. The NIC 150-160 can include, for example, circuitry to support wired communication such as Ethernet, serial, and USB, as well as circuitry to support wireless communication, such as 802.11a/b/g or Bluetooth. Additionally, the NIC 150-160 can support communication between the subsystems 105, 110 as well as the server 115 via a global communication network, such as the Internet. The NIC 150-160 may be part of a motherboard associated with each component 105, 110, 115 or may be provided via a separate plug-in card to maximize flexibility. Any of the components 105, 110, 115 may include memory 165-167, such as CompactFlash™ (commercially available from SanDisk Corporation, Milpitas, Calif.), synchronous dynamic random access memory (SDRAM), and similar memory products as will be appreciated by one of skill in the art, as well as a storage device 168, such as a hard disk drive for long term memory storage, for example.

The NIC circuitry 150 of the detector 105 is responsive to a signal connection at the circuitry 150 order to transfer data from the detector 105 to the system 100 via at least one of the interconnections 135, 140. In one embodiment, the circuitry 150 is responsive to direct physical signal connection with the imaging subsystem 110. In another embodiment, the circuitry 150 is responsive to signal connection to the imaging subsystem 110 via the server 115. In one embodiment, the imaging subsystem 110 is receptive of the data of more than one detector 105 and productive of a signal confirming compatibility of the imaging subsystem 110 with at least one of the more than one detectors 105, based upon the data. Non-limiting examples of data that may be transferred include functionally descriptive properties, image data, text data, waveform data, video data, audio data, and control signals.

The network interconnections 135-145 and NIC 150-160 allow software on the individual subsystems 105, 110 to access the shared resources. Software on the server 115 coordinates with software on the individual subsystems 105-110 to provide access to the shared resources for users in the system 100, or network environment. This software is typically arranged to present the appearance to a user or technician that the subsystems 105, 110 are directly connected.

In an embodiment, the server 115, to which the subsystems 105, 110 are directly attached via interconnections 140, 145, executes software that provides a multi-user operating system. It will be appreciated that in this case the operating system is a "network operating system", as distinguished from a single-user operating system. The software on the individual subsystems 105, 110 and the software on the server 115 have to cooperate with each other to provide access to the shared resources. This may be accomplished by designing the software to use a standardized "protocol" so that multiple vendors can provide interoperable subsystems 105, 110.

It will be appreciated that while an embodiment of the invention has been described having a server 115 as a general-purpose computer on which the server 115 software runs, the scope of the invention is not so limited, and that the invention will also apply to server 115 software that may run on virtual computers that may be part of specialized computers within a medical facility, such as a hospital information system (HIS), a radiology information system (RIS), and picture archiving communication system (PACS), that may be joined within the distributed network system 120 (best seen with reference to FIG. 2) as servers 131-133, for example.

Using the NIC 150, the detector 105 transfers relevant information and data, such as functionally descriptive properties and image data for example, to one or both of the imaging subsystem 110 and the server 115. It will be appreciated that present detectors, integrated within an imaging system with a specific imaging subsystem specifically configured for the integrated detector, lack capability to transfer functionally descriptive properties. As such, use of a present detector with a different imaging subsystem requires extensive configuration of the imaging subsystem. The detector 105, having the memory 165 and/or storage device 168 configured for storing the functionally descriptive properties that describe a functional characteristic of the detector 105, allows for subsequent transfer of the functionally descriptive properties to other components such as the imaging subsystem 110 and server 115. The server 115 is receptive of the functionally descriptive properties of the detector 105 and productive of a signal representative of compatibility of a combination of detector 105 and imaging subsystem 110 based upon the functionally descriptive properties such as dual energy imaging capability, tomosynthesis imaging capability, single energy capability, matrix size, number and location of defective pixels, image read-out rate, calibration data, battery charge, weight and size of the detector 170, image storage capacity, and readiness for use to image, for example.

In one embodiment, the detector 105 transfers image data (such as a signal representative of received attenuated radiation) to the imaging subsystem 110, such as a digital X-Ray imaging subsystem 110 that includes appropriate hardware and/or software to process the image data generated and transferred by the detector 105 to reconstruct a medical image. As an alternative, the detector 105 transfers the image data to the server 115. After receiving the image data from the detector 105, the server 115 processes the data by using hardware and software installed on the server 115 to produce a reconstructed medical image. Alternatively, the server 115 transfers the image data to the imaging subsystem 110 for image reconstruction and processing. It is contemplated that data transfer efficiency is increased by direct transfer of image data generated by the detector subsystem 105 to the imaging subsystem 110 via network interconnection 135, as doing so reduces bandwidth and network data traffic through the server 115. However, it is further contemplated that with future increased network capabilities, network data traffic and bandwidth limitations may be reduced.

In an embodiment, following image data acquisition, image data and associated information is transferred from the detector 105 to the imaging subsystem 110 via network interconnection 135. Alternatively, the image data and associated information is transferred directly to the server 115 via the network interconnection 140, depending on parameters of the imaging system 100 such as traffic, efficiency, and available bandwidth, for example.

In another embodiment, the detector 105 includes diagnostic circuitry to test and determine an operational status of the detector 105, such as battery charge remaining, temperature, and communication link bandwidth for example. In an embodiment, the detector 105 periodically, or when need arises, notifies at least one of the server 115 via the network interconnection 140, or the imaging subsystem 110 via the network interconnection 135 of the operational status of the detector 105. Such information determines functionality of the imaging subsystem 110 with the detector 105 and whether the imaging subsystem 110 can continue to utilize the detector 105, or if the detector 105 requires repair or replacement. Upon a dissociation of the detector 105 from the imaging subsystem 110 (due to technician request or detector 105 failure or power loss for example), a new detector 105 can be associated with the imaging subsystem 110, as will be described below.

An embodiment of the invention may be embodied in the form of computer-implemented processes and apparatuses for practicing those processes. Embodiments of the present invention may also be embodied in the form of a computer program product having computer program code containing instructions embodied in tangible media, such as floppy diskettes, CD-ROMs, hard drives, USB (universal serial bus) drives, or any other computer readable storage medium, wherein, when the computer program code is loaded into and executed by a computer, the computer becomes an apparatus for practicing the invention. Embodiments of the invention also may be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to allow use of interchangeable modular detector subsystems and modular imaging subsystems independent of one another.

As disclosed, some embodiments of the invention may include some of the following advantages: increased flexibility and reduced cost of system design, implementation, application deployment, and servicing as a result of use of modular imaging components; reduced costs of quality, as previously unusable detector panels will be applicable to appropriate applications and procedures; reduced system upgrade costs and obsolescence avoidance provided by the ability to replace only enhanced autonomous components; simplified imaging system use of networked components including availability of multiple types of detectors based on capability; reduced overhead costs by sharing detectors with different imaging subsystems; reduced imaging system downtime by enabling immediate user-replacement of a defective detector panel; reducing workflow delays associated with selection of an incompatible detector for a given application by ensuring compatibility at the time of selection; easier upgrade of advanced applications; increased ease of application upgrades; increased availability of advanced applications to multiple subsystem components; and increased efficiency of scheduling available equipment and applications.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. An autonomous medical imaging system, comprising:
at least one autonomous imaging subsystem comprising an X-ray source; and
at least one autonomous digital X-ray detector comprising a matrix of image pixels, wireless communication circuitry, and a memory, wherein the at least one digital X-ray detector is configured to receive X-ray radiation from the X-ray source and to generate image data, via the matrix of image pixels, based upon the received radiation;

wherein the at least one autonomous digital X-ray detector is configured to transfer both functionally descriptive properties associated with the at least one autonomous digital X-ray detector and the image data to the at least one autonomous imaging subsystem, and wherein the at least one autonomous imaging subsystem is configured to communicate with the at least one autonomous digital X-ray detector, and the functionally descriptive properties describe at least one functional characteristic of the autonomous digital X-ray detector.

2. The autonomous medical imaging system of claim 1, wherein the at least one autonomous digital X-ray detector is configured to communicate with the at least one autonomous imaging subsystem over a network, and wherein the at least one autonomous imaging subsystem is configured to communicate with the at least one autonomous digital X-ray detector over the network.

3. The autonomous medical imaging system of claim 1, wherein the at least one autonomous digital X-ray detector is configured to communicate with the at least one autonomous imaging subsystem over a global communication network (Internet), and wherein the at least one autonomous imaging subsystem is configured to communicate with the at least one autonomous digital X-ray detector over the global communication network.

4. The autonomous medical imaging system of claim 1, further comprising at least one server coupled to the at least one autonomous imaging subsystem and the at least one autonomous digital X-ray detector.

5. The autonomous medical imaging system of claim 4, wherein the at least one server includes at least one processor, memory, at least one storage device, and at least one display.

6. The autonomous medical imaging system of claim 4, wherein the at least one autonomous digital X-ray detector is configured to communicate with the at least one server, and wherein the at least one autonomous imaging subsystem is configured to communicate with the at least one server.

7. The autonomous medical imaging system of claim 6, wherein the at least one autonomous digital X-ray detector is configured to communicate with the at least one server over a network, and wherein the at least one autonomous imaging subsystem is configured to communicate with the at least one server over the network.

8. The autonomous medical imaging system of claim 6, wherein the at least one autonomous digital X-ray detector is configured to communicate with the at least one server over a global communication network (Internet), and wherein the at least one autonomous imaging subsystem is configured to communicate with the at least one server over the global communication network.

9. The autonomous medical imaging system of claim 4, further comprising at least one of:
    a picture archiving communication system;
    a hospital information system;
    a radiology information system; and
    any combinations thereof.

10. The autonomous medical imaging system of claim 1, wherein the autonomous digital X-ray detector is further configured to transfer to the autonomous imaging subsystem at least one of:
    waveform data;
    video data; and
    audio data.

11. The autonomous medical imaging system of claim 10, wherein the functionally descriptive properties comprise at least one of dual energy imaging capability, tomosynthesis imaging capability, matrix size, number of defective image pixels, location of defective image pixels, image read-out rate, calibration data, battery charge, weight and size of the detection subsystem, weight and size of the imaging subsystem, storage capacity, readiness to image, or combinations thereof.

12. An autonomous medical imaging system, comprising:
    an autonomous imaging subsystem comprising an X-ray source; and
    an autonomous digital X-ray detector comprising a matrix of image pixels, wireless communication circuitry, and a memory, wherein the digital X-ray detector is configured to receive X-ray radiation from the X-ray source and to generate image data, via the matrix of image pixels, based upon the received radiation;
    wherein the autonomous digital X-ray detector is configured to transfer both functionally descriptive properties associated with the autonomous digital X-ray detector and the image data to the autonomous imaging subsystem, wherein the autonomous digital X-ray detector communicates with the autonomous imaging subsystem through a global communication network.

13. The autonomous medical imaging system of claim 12, wherein the functionally descriptive properties includes at least one of tomosynthesis imaging capability, matrix size, number of defective image pixels, location of defective image pixels, image read-out rate, calibration data, battery charge, weight and size of the detection subsystem, weight and size of the imaging subsystem, storage capacity, and readiness to image.

14. The autonomous medical imaging system of claim 12, wherein:
    the autonomous digital X-ray detector is further configured to transfer to the autonomous imaging subsystem at least one of:
    waveform data;
    video data; and
    audio data.

15. An autonomous medical imaging system, comprising:
    an autonomous imaging subsystem comprising an X-ray source; and
    an autonomous digital X-ray detector comprising a matrix of image pixels, wireless communication circuitry, a memory, and diagnostic circuitry to test and determine an operational status of the autonomous digital X-ray detector;
    wherein the autonomous digital X-ray detector is configured to send information corresponding to the operational status of the autonomous digital X-ray detector through a global communication network, wherein the information includes at least one of a remaining battery charge associated with the autonomous digital X-ray detector and a temperature associated with the autonomous digital X-ray detector.

* * * * *